United States Patent [19]

Nobbio

[11] Patent Number: Plant 5,767

[45] Date of Patent: Jul. 15, 1986

[54] CARNATION NAMED DOLCEDO

[76] Inventor: Giacomo Nobbio, Strada Villetta 5, San Remo, Imperia, Italy

[21] Appl. No.: 600,942

[22] Filed: Apr. 16, 1984

[51] Int. Cl.[4] ..... A01H 5/00
[52] U.S. Cl. ..... Plt./71
[58] Field of Search ..... Plt./71

*Primary Examiner*—James R. Feyrer
*Attorney, Agent, or Firm*—Charles W. Rummler

[57] ABSTRACT

A new carnation cultivar, substantially as herein shown and described, characterized by its unifloral production of double type flowers having much more than normal number of petals, each of which has a monochrome distribution of a very light pink color, the blooms having exceptional endurance as cut flowers, good suitability for shipment and the plant itself being particularly well suited to commercial greenhouse cultivation for the production of cut flowers.

1 Drawing Figure

BACKGROUND OF THE NEW PLANT

My new carnation cultivar was originated in 1979 as a seedling, at my breeding establishment in San Remo, Italy, which resulted from my crossing of the carnation variety known as "Faust" as the seed parent, with an unnamed pink carnation identified in my records under U.S. Plant Pat. No. 8,367 as the pollen parent, this particular seedling having been selected because of the very large size of its double type flower, symmetrical form, and very light pink coloration, the plant itself appearing to have good growth characteristics with long stems of sturdy size and well suited to commercial greenhouse cultivation for the production of cut flowers.

Repeated trials of propagation, by means of cuttings and through several successive generations, has demonstrated conclusively that the novel characteristics of this new carnation variety hold true from generation to generation and appear to be firmly fixed.

DESCRIPTION OF THE DRAWING

My new carnation cultivar is illustrated by the accompanying full color photographic drawing, which shows the inflorescence of a fully grown plant, the view including buds, a newly opened flower, a face view of a fully developed flower, specimens of the flower petals, and a specimen of an unpinched stem, the colors shown being as nearly true as it is reasonably possible to obtain by means of conventional photographic procedures considering the arrangement of the specimens for photographic purposes.

DESCRIPTION OF THE NEW PLANT

The following is a detailed description of my new carnation variety based upon observation of plants grown under conventional greenhouse procedures, the color designations being according to The R.H.S. Colour Chart published by The Royal Horticultural Society of London, England.

THE PLANT

Origin: Seedling.
Parentage:
*Seed parent.*—The variety known as "Faust".

*Pollen parent.*—An unnamed pink variety identified in my records under U.S. Plant Pat. No. 8,367.

Classification:
*Botanic.*—*Dianthus caryophyllus.*
*Commercial.*—Greenhouse carnation for cut flower production.

Form: Herbaceous bush having long stems with total length of seven internodes.

Growth: Upright and vigorous.

Branching: Normal and medium in number. The original stem is pinched at a height of about 10 or 12 cm. from the base after it has reached a height of about 30 cm. in order to promote the production of about 4 or 5 lateral shoots which grow rapidly and branch freely. These stems and their branches may be pinched or pruned according to the desired length of the flower stem, in any case the flower being terminal.

Foliage:
*Quantity.*—Moderate.
*Leaf size.*—Medium in both length and breadth.
*Leaf shape.*—Linear with acuminate apex and entire margins.
*Texture.*—Smooth.
*Color.*—Green.

THE BUD

Size: Large.

Form: Ovoid immediately before color appears, becoming bell-shaped upon opening.

Sepals:
*Condition.*—Upstanding, broad and with cuspidate form of tip.

Calyx:
*Size.*—Medium.
*Shape.*—As of a truncated cone.
*Aspect.*—Smooth.
*Splitting.*—The calyx does not split.

Peduncle: Rigid and erect.

THE FLOWER

Blooming habit: Continuous.

Size of bloom: Very large and of double type.

Borne: Singly on strong, upright stems.

Shape: Symmetrical with bunched cupule when in full bloom.

Petalage:

*Number of petals.*—More than 80.
*Shape.*—Generally fan-shaped with laciniate margin.
*Color.*—R.H.S. 36B.
*Distribution of color.*—Monochrome.
*Texture.*—Soft.
*Appearance.*—Satiny.
*Fragrance.*—Absent or very faint.
*Persistence.*—The petals hang on and dry.

Lasting quality:
*As a cut flower.*—Exceptional.
*Suitability for shipment.*—Very good.

REPRODUCTIVE ORGANS

Androecium: Absent during the winter period.

Stamens:
*Number.*—1 or 2, but not in every flower and only in summer.
*Anthers.*—Size: Normal. Color: Cream.
*Filaments.*—Length: 1 to 1.5 cm. Color: White.
*Pollen.*—Color: White.

Pistils: More than two in number.
*Number.*—4 to 8.
*Styles.*—Color: Cream, lightly shaded with green.
*Pollen.*—Color: White.
*Stigmas.*—Smooth surface and having a cream color.

Ovary: Long, ribbed and irregular in shape.

This new variety of carnation is distinguished by its unusual very light pink flowers having petals that are deeply laciniated to the extent of about 13 mm., the flower having exceptional endurance and good stability for shipment as cut flowers thus making this new plant particularly well suited to commercial greenhouse cultivation for the production of cut flowers.

I claim:

1. The new and distinct carnation variety, substantially as herein shown and described, characterized by its very large light pink flowers of the double type and having a greater than normal number of petals of monochrome coloration and deeply laciniated margins.

* * * * *

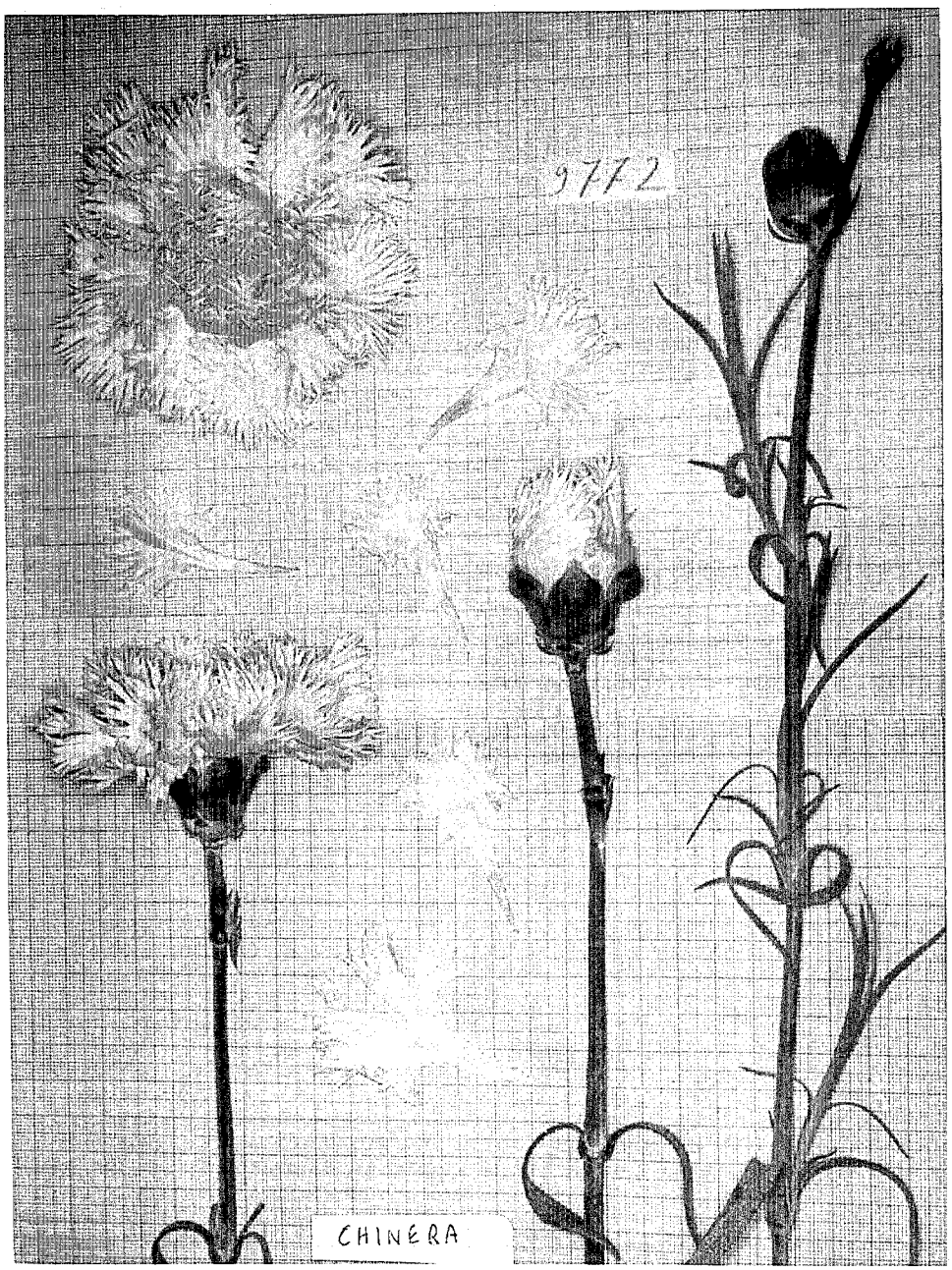
9772
CHINERA

UNITED STATES PATENT AND TRADEMARK OFFICE

CERTIFICATE OF CORRECTION

PATENT NO. : Plant 5,767

DATED : July 15, 1986

INVENTOR(S) : Giacomo Nobbio

It is certified that error appears in the above-identified patent and that said Letters Patent are hereby corrected as shown below:

Column 1, line 6, delete "U.S. Plant Pat.".

Column 2, line 2, delete "U.S. Plant Pat.".

The title should be: CARNATION NAMED CHINERA.

Signed and Sealed this

Eleventh Day of November, 1986

*Attest:*

DONALD J. QUIGG

*Attesting Officer*

*Commissioner of Patents and Trademarks*